US011433048B2

(12) United States Patent
Pietrancosta et al.

(10) Patent No.: US 11,433,048 B2
(45) Date of Patent: Sep. 6, 2022

(54) CXCR4 RECEPTOR-BINDING COMPOUNDS USEFUL FOR INCREASING INTERFERON LEVEL

(71) Applicants: CENTRE NATIONAL de la RECHERCHE SCIENTIFIQUE, Paris (FR); UNIVERSITE PARIS DESCARTES, Paris (FR)

(72) Inventors: Nicolas Pietrancosta, Paris (FR); Nikaïa Smith, Nice (FR); Jean-Philippe Herbeuval, Paris (FR)

(*) Notice: Subject to any disclaimer, the term of this patent is extended or adjusted under 35 U.S.C. 154(b) by 0 days.

(21) Appl. No.: 16/310,149

(22) PCT Filed: Jun. 16, 2017

(86) PCT No.: PCT/EP2017/064832
§ 371 (c)(1),
(2) Date: Dec. 14, 2018

(87) PCT Pub. No.: WO2017/216373
PCT Pub. Date: Dec. 21, 2017

(65) Prior Publication Data
US 2019/0175549 A1 Jun. 13, 2019

(30) Foreign Application Priority Data
Jun. 16, 2016 (FR) .................................. 16305736.7

(51) Int. Cl.
| | | |
|---|---|---|
| *A61K 31/395* | (2006.01) | |
| *A61K 31/4725* | (2006.01) | |
| *G16C 20/64* | (2019.01) | |
| *G16B 35/20* | (2019.01) | |
| *A61K 31/4164* | (2006.01) | |
| *A61K 31/417* | (2006.01) | |
| *A61K 31/4709* | (2006.01) | |
| *G01N 33/566* | (2006.01) | |
| *G01N 33/68* | (2006.01) | |

(52) U.S. Cl.
CPC .......... *A61K 31/395* (2013.01); *A61K 31/417* (2013.01); *A61K 31/4164* (2013.01); *A61K 31/4709* (2013.01); *A61K 31/4725* (2013.01); *G01N 33/566* (2013.01); *G01N 33/6866* (2013.01); *G16B 35/20* (2019.02); *G16C 20/64* (2019.02)

(58) Field of Classification Search
CPC .............. A61K 31/395; A61K 31/4164; A61K 31/417; A61K 31/4709; A61K 31/4725; G01N 33/566; G16B 35/20; G16C 20/64
USPC ........................................................ 544/188
See application file for complete search history.

(56) References Cited

U.S. PATENT DOCUMENTS

| | | | | |
|---|---|---|---|---|
| 6,987,102 B2* | 1/2006 | Bridger | ................. | A61K 31/33 |
| | | | | 514/183 |
| 7,897,590 B2* | 3/2011 | Bridger | .................. | A61P 17/02 |
| | | | | 514/183 |
| 2005/0154005 A1* | 7/2005 | Bridger | ................ | C04B 35/632 |
| | | | | 514/291 |
| 2008/0287454 A1* | 11/2008 | Bridger | ................ | C04B 35/632 |
| | | | | 514/252.13 |

FOREIGN PATENT DOCUMENTS

| | | |
|---|---|---|
| WO | 2000/02870 | 1/2000 |
| WO | 2000/66112 | 11/2000 |
| WO | 2001/44229 | 6/2001 |
| WO | 2003/055876 | 7/2003 |
| WO | 2006/020415 | 2/2006 |
| WO | 2006/039250 | 4/2006 |

OTHER PUBLICATIONS

Public summary of opinion on orphan designation; Feb. 23, 2015 EMA/COMP/735793/2014—Committee for Orphan Medicinal Products Plerixafor for the treatment of WHIM syndrome.*
Davies, S.L et al., Drugs of the Future, 2007, vol. 32, pp. 123-136.*
DeClerq, E. Nat. Rev. Drug Discov. 2003, vol. 2, pp. 581-587.*
Lukacs, N. et al., Am. J. Pathol. 2002, vol. 160, pp. 1353-1358.*
Nicholas w. lukacs et al, (2002) The American journal of pathology, 160: 1353-1360, (XP055189120).
De Clercq, (2003), Nature reviews, drug discovery, 2: 581 587 (XP002683304).
Davies et al,(2007) Drugs of the future, 32, p. 123, (XP055068423).
Este J A et al, (1999) Molecular pharmacology, 55: 67-73 (XP008038631).
Gary J. Bridger et al, (1999) Journal of medicinal chemistry, 42: 3971-3981, (XP055113935).
Gary J. Bridger et al, (2010) Journal of medicinal chemistry, 53: 1250-1260, (XP055325240).
Jerry S. Hu et al, American journal of pathology, 169: 424-432 (XP055324773).
Skerlj et al, (2010) Journal of medicinal chemistry, 53: 3376-3388 (XP055047306).
Chongqian Zhang et al, (2014) Chemical biology & drug design, 85: 119-136, (XP055325266).
Xian-Ming Xia, (2010) World journal of gastroenterology, 16: 2873, (XP055316548).

* cited by examiner

*Primary Examiner* — Heidi Reese
(74) *Attorney, Agent, or Firm* — Wolter VanDyke Davis PLLC; Michael Byrne (57) ABSTRACT

The invention relates to a CXCR4 receptor-binding compound for use for increasing or restoring interferon (IFN) level in an individual, wherein the interferon is a type-I interferon (IFN-I).

7 Claims, 2 Drawing Sheets
Specification includes a Sequence Listing.

SEQUENCE LISTING

<160> NUMBER OF SEQ ID NOS: 15

<210> SEQ ID NO 1
<211> LENGTH: 352
<212> TYPE: PRT
<213> ORGANISM: Homo sapiens

<400> SEQUENCE: 1

Met Glu Gly Ile Ser Ile Tyr Thr Ser Asp Asn Tyr Thr Glu Met
1               5                   10                  15

Gly Ser Gly Asp Tyr Asp Ser Met Lys Glu Pro Cys Phe Arg Glu Glu
            20                  25                  30

```
Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
 50                  55                  60

Tyr Gln Lys Lys Leu Arg Ser Met Thr Asp Lys Tyr Arg Leu His Leu
 65                  70                  75                  80

Ser Val Ala Asp Leu Leu Phe Val Ile Thr Leu Pro Phe Trp Ala Val
                 85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
            130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
            195                 200                 205

Ile Leu Pro Gly Ile Val Ile Leu Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
gctgaagcag atgcaggaca a                                           21

<210> SEQ ID NO 3
<211> LENGTH: 21
<212> TYPE: DNA
<213> ORGANISM: Artificial
<220> FEATURE:
```

```
<223> OTHER INFORMATION: PCR primer

<400> SEQUENCE: 3
tgacggagtt gccacttgac t                                              21

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
ccagttccag aaggctccag                                                20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
tcctcctgca tcacacaggc                                                20

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
cccacagcct gggtaatagg a                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
cagcagatga gtcctctgtg c                                              21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tgcattacct gaaggccaag g                                              21

<210> SEQ ID NO 9
<211> LENGTH: 21
<212> TYPE: DNA
<213> ORGANISM: Artificial
<220> FEATURE:
<223> OTHER INFORMATION: PCR primer

<400> SEQUENCE: 9
agcaattgtc cagtcccagt g                                              21
```

```
<210> SEQ ID NO 10
<211> LENGTH: 21
<212> TYPE: DNA
<213> ORGANISM: Artificial
<220> FEATURE:
<223> OTHER INFORMATION: PCR primer

<400> SEQUENCE: 10
ggcagccaac ctaagcaaga t                                              21

<210> SEQ ID NO 11
<211> LENGTH: 21
<212> TYPE: DNA
<213> ORGANISM: Artificial
<220> FEATURE:
<223> OTHER INFORMATION: PCR primer

<400> SEQUENCE: 11
cagggtcacc tgacacattc a                                              21

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
taaccacccc tgacccaacc                                                20

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
atttgccgaa gagccctcag                                                20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
aggacaggaa gctgaaggag                                                20

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
agtgggtgtt tcctgcaagg                                                20
```

CXCR4 RECEPTOR-BINDING COMPOUNDS USEFUL FOR INCREASING INTERFERON LEVEL

CROSS-REFERENCE TO RELATED APPLICATIONS

This application is a U.S. national phase of International Application No. PCT/EP2017/064832 filed Jun. 16, 2017, which claims the benefit of French Application No. 16305736.7 filed Jun. 16, 2016, the entire contents of which are hereby incorporated by reference.

SEQUENCE LISTING

This application contains a Sequence Listing which has been submitted in ASCII format entitled "B000057WOSequenceListing.txt" via EFS-Web and is hereby incorporated by reference in its entirety.

FIELD OF THE INVENTION

The invention relates to compounds for use for increasing, in particular restoring, interferon (IFN) level in an individual.

BACKGROUND OF THE INVENTION

There are numerous situations where increasing or restoring interferon level, especially type I interferon level, can be beneficial for an individual.

This may be the case for a viral infection of course, but also for certain autoimmune diseases such as type-I diabetes, rheumatoid arthritis or multiple sclerosis, as well as diabetes, allergy or cancer.

Indeed, it has been shown that there was a reduced secretion of IFN-a by blood dendritic cells in human diabetes (Summer et al. (2006) Clinical Immunology, 121:81-89). Besides, recombinant type I interferon (IFN-I), especially IFN-β, is currently used as a treatment for multiple sclerosis, in particular relapsing multiple sclerosis (Weinstock-Guttman (2008) *Expert Opin Biol Ther* 8:1435-1447).

However, its use requires frequent subcutaneous or intramuscular injections, from every other day to every two weeks for the most recent pegylated form of IFN-β (Plegridy®), rendering the treatment difficult to follow for the treated individuals. Besides, as with most treatment with recombinant proteins, individuals often develop an immune response against the administered protein which diminishes the effectivity of the treatment on the long run.

It is thus an aim of the present invention to provide compounds for increasing or restoring IFN level, in particular IFN-I, in an individual overcoming these problems.

SUMMARY OF THE INVENTION

The present invention arises from the unexpected finding by the inventors that AMD3100 treatment could restore Type I interferon production by HIV-activated plasmacytoid dendritic cells inhibited by other compounds.

Thus, the present invention relates to a CXCR4 receptor-binding compound for use for increasing, in particular restoring, interferon (IFN) level in an individual, in particular type-I interferon (IFN-I) level, more particularly interferon-alpha (IFN-a) and/or interferon-beta (IFN-β) level.

The present invention also relates to the CXCR4 receptor-binding compound for use according to the invention, for increasing, in particular restoring, interferon (IFN) secretion, in particular type-I IFN secretion, more particularly IFN-a and/or IFN-β secretion, by immune cells, in particular plasmacytoid dendritic cells, monocytes or Natural Killer (NK) cells.

The invention also relates to the CXCR4 receptor-biding compound for use according to the invention in the prevention or treatment of a disease selected from the group consisting of a viral infection, an opportunistic infection, allergy, rheumatoid arthritis, multiple sclerosis, a cancer with an overproduction of spermine, depression-induced immunosuppression and diabetes.

The present invention also relates to a method for increasing, or restoring, interferon (IFN) level, in particular type-I IFN level, more particularly IFN-a and/or IFN-β level, in an individual, comprising administering to the individual an effective amount of at least one CXCR4 receptor-binding compound.

The present invention also relates to a method for increasing, in particular restoring, IFN secretion, in particular type-I IFN secretion, more particularly IFN-a and/or IFN-β secretion, by immune cells, in particular plasmacytoid dendritic cells, monocytes and NK cells in an individual, comprising administering to the individual an effective amount of at least one CXCR4 receptor-binding compound.

The present invention further relates to a method for the prevention or treatment of a disease selected from the group consisting of a viral infection, an opportunistic infection, allergy, rheumatoid arthritis, multiple sclerosis, a cancer with an overproduction of spermine, depression-induced immunosuppression and diabetes, comprising administering to the individual a prophylactically or therapeutically effective amount of at least one CXCR4 receptor-binding compound according to the invention.

The invention also relates to the in vitro use of a CXCR4 receptor-binding compound according to the invention, for increasing, in particular restoring, IFN secretion, in particular type-I IFN secretion, more particularly IFN-a and/or IFN-β secretion, by plasmacytoid dendritic cells, monocytes and NK cells.

The invention also relates to an in vitro screening method for identifying compounds for increasing, in particular restoring, IFN secretion, in particular type-I IFN secretion, more particularly IFN-a and/or IFN-β secretion, in an individual from candidate compounds, wherein the candidate compounds are CXCR4 receptor-binding compounds according to the invention.

The invention also relates to an in vitro screening method for identifying compounds for increasing, in particular restoring, IFN secretion, in particular type-I IFN secretion, more particularly IFN-a and/or IFN-β secretion, in an individual from candidate compounds, comprising:

binding a CXCR4 receptor with a detectable CXCR4 receptor-binding compound according to the invention;

contacting the CXCR4 receptor bound to the detectable CXCR4 receptor-binding compound with a candidate compound;

selecting the candidate compound which increase the binding of the detectable CXCR4 receptor-binding compound to the CXCR4 receptor, thereby identifying a compound for restoring IFN level.

The invention also relates to an in vitro screening method for identifying compounds for increasing, in particular restoring, IFN level in particular type-I IFN level, more particularly IFN-a and/or IFN-β level, in an individual from candidate compounds, comprising the steps of:

contacting blood cells with a candidate compound;
determining the level of secretion of IFN by the contacted blood cells;
comparing the determined level of secretion of IFN to the level of expression of IFN by blood cells contacted by a reference compound;
selecting the candidate compound which have a decreased, increased or similar level of expression of IFN with respect to the reference compound, thereby identifying a compound for increasing IFN level,
wherein the reference compound is a CXCR4 receptor-binding compound according to the invention, in particular AMD3100.

The invention also relates to an in silico method for screening compounds from candidate compounds, or for designing compounds, for increasing, in particular restoring, IFN level, in particular type-I IFN level, more particularly IFN-α and/or IFN-β level, in an individual, comprising a computer-implemented step of determining if a designed compound or a candidate compound interacts with at least 6 amino acids of a CXCR4 receptor represented by SEQ ID NO: 1, wherein the amino acids are selected from the group consisting of alanine 175, aspartic acid 171, aspartic acid 262, phenylalanine 174, valine 196, glycine 207, tyrosine 255, tyrosine 256, isoleucine 259, serine 263 and glutamic acid 288.

DETAILED DESCRIPTION OF THE INVENTION

As intended herein, the term "comprising" has the meaning of "including" or "containing", which means that when an object "comprises" one or several elements, other elements than those mentioned may also be included in the object. In contrast, when an object is said to "consist of" one or several elements, the object is limited to the listed elements and cannot include other elements than those mentioned.

CXCR4 Receptor-Binding Compound

As known in the art, the "CXCR4 receptor" is the C-X-C chemokine receptor type 4 also known as fusin or CD184. As intended herein, the expression "CXCR4 receptor" is equivalent to "CXCR4". Preferably, the CXCR4 receptor according to the invention is a human CXCR4 receptor. CXCR4 is notably represented by SEQ ID NO: 1.

A CXCR4 receptor-binding compound according to the invention can either be known in the art to bind to CXCR4 or it can be determined that it binds to CXCR4. Determining that a compound binds to CXCR4 can be performed by numerous ways known to one of skill in the art. By way of example, CXCR4 binding is assessed by flow cytometry analysis. This procedure is explained in more details in the following Example.

Preferably, the CXCR4 receptor-binding compound according to the invention comprises from 1 to 45 carbon atoms and at least one amine group positively charged at a pH from 6 to 8, in particular at a pH from 7.0 to 7.8, more particularly at a physiological blood pH of a human individual.

Preferably, the CXCR4 receptor-binding compound according to the invention interacts with at least 5, 6, 7, 8, 9, 10 or 11 amino acids of a CXCR4 receptor represented by SEQ ID NO: 1, wherein the amino acids are selected from the group consisting of alanine 175, aspartic acid 171, aspartic acid 262, phenylalanine 174, valine 196, glycine 207, tyrosine 255, tyrosine 256, isoleucine 259, serine 263 and glutamic acid 288.

The above-defined amino acids have been identified by the present inventors as defining the binding site on the CXCR4 receptor responsible for increasing, in particular restoring, IFN secretion by immune cells, in particular plasmacytoid dendritic cells, monocytes and NK cells. Besides, as should be clear to one of skill in the art, SEQ ID NO: 1 is only meant as a reference sequence to unequivocally define the positions of the amino acids of the CXCR4 receptor involved in the binding of the CXCR4 receptor-binding compound according to the invention. Accordingly, SEQ ID NO: 1 is not meant to limit the CXCR4 receptors according to the invention. Indeed, the CXCR4 receptor-binding compounds according to the invention can also bind to the above-defined amino acids in variants, mutants or truncated forms of the CXCR4 receptor or in proteins or polypeptides comprising the CXCR4 receptor, which may change the absolute position of the amino acids in said variants, mutants or truncated forms or proteins or polypeptides, but not their function.

The CXCR4 receptor-binding compound according to the invention may in particular be a natural amine or a synthetic amine, a monoamine or a polyamine.

In an embodiment, the CXCR4 receptor-binding compound according to the invention is a compound of the following formula (I):

$$Z-R-A-R'-Y \qquad (I)$$

wherein:
Z and Y, which are identical or different, represent:
an alkyl group having from 1 to 6 carbon atoms, optionally substituted by a hydroxyl group, an ethylene, a halogen atom, a CN group, a $CF_3$ group, a SO group, a $NO_2$ group, an amine group, a difluor or an alkyl, S-alkyl or O-alkyl group having from 1 to 6 carbon atoms, or
an aryl or heteroaryl group having from 3 to 6 carbon atoms, optionally substituted by a hydroxyl group, an ethylene, a halogen atom, a CN group, a $CF_3$ group, a SO group, a $NO_2$ group, an amine group, a difluor or an alkyl, S-alkyl or O-alkyl group having from 1 to 6 carbon atoms, or
a cyclic or heterocyclic polyamine group having from 9 to 32 ring members and from 3 to 8 amine groups in the ring spaced by 2 or more carbon atoms from each other, optionally comprising an aryl or heteroaryl group having from 3 to 6 carbon atoms, a heteroatom or a heteroelement, and optionally substituted by a halogen atom, a hydroxyl group, a heteroatom, a heteroelement, an alkyl, S-alkyl or O-alkyl group having from 1 to 6 carbon atoms or an aryl or heteroaryl group having from 3 to 6 carbon atoms, and
A represents an aryl or heteroaryl group having from 3 to 12 carbon atoms, and
R and R', which are identical or different, represent an alkyl group having from 1 to 6 carbon atoms or a $R_1NR_2R_3$ group, and
$R_1$ represents a single bond or an alkyl group having from 1 to 6 carbon atoms, and
$R_2$ and $R_3$, which are identical or different, represent a hydrogen atom, an amine group, an alkyl group having from 1 to 6 carbon atoms or an aryl or heteroaryl group having from 3 to 6 carbon atoms, optionally substituted by an alkyl group having from 1 to 6 carbon atoms,
or a pharmaceutically acceptable salt and/or hydrate thereof.

Preferably, the compound of formula (I) as defined above is selected form the compounds shown in FIG. 17 and FIG. 18 of the article of Debnath et al. (2013) *Theranostics* 3:47-75.

More preferably, the compound of formula (I) as defined above is selected form the group consisting of:

and

Preferably, the CXCR4 receptor-binding compound according to the invention is a compound of formula (I), wherein:

Z and Y are identical and represent cyclic polyamine moieties having from 9 to 20 ring members and from 3 to 6 amine groups in the ring spaced by 2 or more carbon atoms from each other, and A represents an aromatic or heteroaromatic group having from 3 to 8 carbon atoms, and

R and R', which are identical or different, represent a methylene linked to a nitrogen atom of Z or Y, the nitrogen atoms being otherwise unsubstituted.

Preferably, the compound of formula (I) as defined above is plerixafor:

Compound of formula (I) according to the invention can be readily synthesized by one of skill in the art, as is in particular described in international application WO204/125499.

In still another embodiment, the CXCR-4 receptor-binding compound according to the invention is a compound of the following formula (II):

(II)

wherein:
D$_1$ and D$_2$, which may be identical or different, represent:
an alkyl group having from 1 to 6 carbon atoms optionally substituted by at least one hydroxyl group, a halogen atom, a CF$_3$ group, a CN group, an amine group, or an alkyl, O-alkyl or S-alkyl group having from 1 to 12 carbon atoms, or
an aryl, an heteroaryl, a cycloalkyl, a heterocycloalkyl, an alkylaryl, an alkylheteroaryl, or an alkylheteropolyaryl group having from 3 to 12 carbon atoms, optionally substituted by at least one hydroxyl group, halogen atom, CF$_3$ group, CN group, amine group, or alkyl, O-alkyl or S-alkyl group having from 1 to 12 carbon atoms, or
D$_1$ and D$_2$ are linked together to form a N-containing aryl or heteroaryl group having from 3 to 12 carbon atoms and optionally substituted by at least one amine group optionally substituted by an alkylheteroaryl, group having from 3 to 12 carbon atoms, and
X represents:
an alkyl group having from 1 to 6 carbon atoms, or
—R$_4$—Y—R$_5$— wherein, R$_4$ and R$_5$ which are identical or different represent an alkyl group having from 1 to 6 carbon atoms and Y represents an aryl or heteroaryl group having from 3 to 6 carbon atoms, optionally substituted by a halogen atom, a hydroxyl group, an amide group, an amine group, an alkoxy group, an ester group, a CF$_3$ group, a CN group or an alkyl, O-alkyl or S-alkyl group having from 1 to 6 carbon atoms optionally substituted by a hydroxyl group, an amine group or an O-alkyl having from 1 to 6 carbon atoms,
or a pharmaceutically acceptable salt and/or hydrate thereof.

Preferably, the compound of formula (II) as defined above is selected form the compounds shown in FIGS. 9 and 16 of the article of Debnath et al. (2013) *Theranostics* 3:47-75.

More preferably, the compound of formula (II) as defined above is represented by the following formula (III):

(III)

wherein:
E$_1$ represents an alkyl group having from 1 to 12 carbon atoms, or a heteroaryl group having from 3 to 12 carbon atoms, and
E$_2$ represents a heteroalkyl group having from 1 to 12 carbon atoms, substituted by an amine group, and
E$_3$ represents a heteroalkyl group having from 1 to 12 carbon atoms;

or a pharmaceutically acceptable salt and/or hydrate thereof.

Most preferably, the compound of formula (II) as defined above is selected form the group consisting of compounds represented by the following structures:

and

Preferably, the CXCR4 receptor-binding compound according to the invention is a compound of formula (II) as defined above wherein:

$D_1$ and $D_2$, which may be identical or different, represent an aryl or heteroaryl group having from 3 to 12 carbon atoms, optionally substituted by a hydroxyl group or an alkyl group having from 1 to 6 carbon atoms, and X represents an alkyl group having from 1 to 6 carbon atoms, or a pharmaceutically acceptable salt and/or hydrate thereof.

Preferably, the compound of formula (II) according to the invention is AMD070:

Compounds of formula (II) according to the invention can be readily synthesized by one of skill in the art, as is in particular described in Skerlj et al. (2011) *Bioorg. Med. Chem. Lett.*, 21:1414-8.

The pharmaceutically acceptable salt and/or hydrate of compounds of formula (I) and (II) will appear obviously to one of skill in the art. Preferably, the pharmaceutically acceptable salt and/or hydrate of compounds of formula (I) and (II) is selected from the group consisting of hydrobromide, hydrochloride, dihydrobromide, dihydrochloride and metallic salts such as $Zn^{2+}$ salt and $Cu^{2+}$ salt.

As intended herein, the term "alkyl" refers to linear, branched or cyclic alkyl groups.

As intended herein, the term "aryl" denotes an aromatic group comprising at least one aromatic ring.

As intended herein, the term "heteroaryl" denotes an aryl comprising at least one heteroatom preferably selected from the group consisting of O, P, N, S and Si, which is more preferably N.

As intended herein, the term "heteroalkyl", in particular "heterocycloalkyl", denotes an alkyl, in particular a cycloalkyl, comprising at least one heteroatom preferably selected from the group consisting of O, P, N, S and Si, which is more preferably N.

As intended herein the term "alkylaryl" denotes an alkyl group substituted by at least one aryl group.

As intended herein the term "arylalkyl" denotes an aryl group substituted by at least one alkyl group.

The halogen atom according to the invention can be of any type known to one of skilled in the art. Preferably, the halogen atom according to the invention is selected from the group consisting of F, Cl, Br and I.

Preferably, the CXCR-4 receptor-binding compound according to the invention is selected from the group consisting of plerixafor and AMD070. Plerixafor is known in the art as a CXCR4 antagonist and is also referred as to AMD3100 and JM3100. These compounds are represented by the following structures:

Plerixafor

AMD070

Prevention and Treatment

Preferably, the interferon according to the invention is selected from the group consisting of a type I interferon, also denoted IFN-I, a type II interferon, also denoted IFN-II, and a type III interferon, also denoted IFN-III. More preferably, the IFN according to the invention is selected from the group consisting of IFN-a (IFN-alpha, type I), IFN-β (IFN-beta, type I), IFN-γ (IFN-gamma, type II), IFN-λ (IFN-lambda, type III) IFN-ω (IFN omega, type I). Most preferably, the interferon according to the invention is selected from IFN-a and IFN-β.

Preferably, the prevention or treatment according to the invention relates to the prevention or treatment of a disease or a disorder selected from the group consisting of a viral infection, an opportunistic infection, allergy, cancer, in particular with an overproduction of spermine, depression-induced immunosuppression, diabetes, in particular type-I or type-II diabetes, rheumatoid arthritis and multiple sclerosis.

The viral infection according to the invention can be of any type known to one of skill in the art. Preferably, the viral infection according to the invention is dengue.

Opportunistic infections are well known to one of skill in the art and are notably infections caused by pathogens such as bacteria, viruses, fungi or protozoa. Preferably, opportunistic infections according to the invention are selected from the group consisting of tuberculosis, pneumonia, toxoplasmosis, cytomegalovirus infection, and *candida*.

Allergy are well known to one of skill in the art and are notably defined with codes D69, J30, J45, L23, L50, T78.4, Z88 and Z91 of the 10th revision of the International Classification of Diseases (ICD-10) 2016 version by the World Health Organization.

The cancer prevented or treated according to the invention can be of any type known to one of skill in the art. Preferably, the cancer prevented or treated according to the invention is selected from the group consisting of prostate cancer, breast cancer, lung cancer, uterus cancer, digestive system-related cancer, such as colorectal cancer, melanoma and renal cancer. Preferably, the cancer prevented or treated according to the invention is a cancer with an overproduction of spermine.

Immunosuppression prevented or treated according to the invention can be of any type known to one of skill in the art. Preferably, the immunosuppression prevented or treated according to the invention is associated to other pathologies such as infectious diseases, chronic infections, invalidating diseases or associated to treatments such as corticoids, anti-inflammatories, or immunosuppressants. More preferably, the depression prevented or treated according to the invention is a depression-induced immunosuppression.

Rheumatoid arthritis is defined in ICD-10 with codes M05, M06, M08 and multiple sclerosis is defined in ICD-10 with the code G35.

Diabetes prevented or treated according to the invention can be of any type known to one of skill in the art. Diabetes prevented or treated according to the invention are in particular type-I or type-II diabetes.

Preferably, the prevention or treatment according to the invention relates to the prevention of treatment of a disease or a disorder selected from the group consisting of a viral infection, an opportunistic infection, cancer with an overproduction of spermine, depression-induced immunosuppression, diabetes, in particular type-I or type-II diabetes and multiple sclerosis.

Preferably, the prevention or treatment according to the invention relates to the prevention or treatment of a disease or a disorder selected from the group consisting of dengue, tuberculosis, pneumonia, toxoplasmosis, cytomegalovirus infection, *candida*, cancer with an overproduction of spermine and depression-induced immunosuppression.

As should be clear to one of skill in the art, the diseases or disorders according to the invention are prevented or treated by increasing, in particular restoring, interferon (IFN) level, notably type I, II or III interferon (IFN-I, IFN-II, IFN-III). Preferably, the diseases or disorders according to the invention are prevented or treated by increasing, in particular restoring, type-I IFN, more particularly IFN-a and/or IFN-β, level.

Preferably, the level of interferon (IFN), in particular the level of type-I IFN, more particularly the level of IFN-a and/or IFN-β, is increased, in particular restored, by the CXCR4 receptor-binding compound according to the invention, by increasing, in particular restoring, IFN secretion, in particular type-I IFN secretion, more particularly IFN-a and/or IFN-β secretion, by immune cells, in particular plasmacytoid dendritic cells, monocytes and NK cells.

Individual

The individual according to the invention is preferably a mammal, more preferably a human.

Preferably, the individual according to the invention is in need of an increase of IFN, in particular IFN-I, IFN-II or IFN-III. More preferably, the individual according to the invention is in need of an increase of IFN-a and/or IFN-β.

In an embodiment of the invention the individual according to the invention has a normal level of IFN, in particular IFN-I, IFN-II or IFN-III.

The individual according to the invention has preferably, at least one symptom of a disease or disorder or suffers from a disease or disorder selected form the group consisting of a viral infection, an opportunistic infection, allergy, cancer, in particular with an overproduction of spermine, depression-induced immunosuppression, rheumatoid arthritis, diabetes and multiple sclerosis.

In a particular embodiment, the individual according to the invention does not suffer from HIV-infection, rheumatoid arthritis and pulmonary allergy, in particular pulmonary inflammation and hyperactivity of the respiratory tract.

In a particular embodiment, the individual according to the invention does not suffer from opportunistic infection, multiple sclerosis and diabetes.

Administration

Preferably, the CXCR4 receptor-binding compound according to the invention is administered in an effective amount for increasing, in particular restoring, interferon level in an individual.

Preferably also, the CXCR4 receptor-binding compound according to the invention is administered in an effective amount for increasing, in particular restoring, interferon level by immune cells, in particular plasmacytoid dendritic cells, monocytes and NK cells in an individual.

Preferably also, the CXCR4 receptor-binding compound according to the invention is administered in a prophylactically or therapeutically effective amount for preventing or treating a disorder selected from the group consisting of viral infection, an opportunistic infection, allergy, cancer, in particular with an overproduction of spermine, depression-induced immunosuppression, rheumatoid arthritis diabetes and multiple sclerosis.

The CXCR4 receptor-binding compound according to the invention can be administered by any route known in the art, such as the intravenous, intramuscular, subcutaneous injection, oral, or topical routes.

In Vitro Screening Methods

Preferably, the in vitro screening method for identifying compounds for increasing, in particular restoring, IFN secretion, in particular type-I IFN secretion, more particularly IFN-a and/or IFN-β secretion, in an individual from candidate compounds, wherein the candidate compounds are CXCR4 receptor-binding compounds according to the invention comprises the steps of:
- contacting blood cells with a candidate compound;
- determining the level of secretion of IFN by the contacted blood cells;
- selecting the candidate compound which increases the level of secretion of IFN with respect to the level of secretion of IFN before the blood cells have been contacted by the candidate compound, thereby identifying a compound for increasing, in particular restoring, IFN level.

Preferably, the in vitro screening method according to the invention is performed by flow cytometry.

Blood cells according to the invention can be of any type known to one of skilled in the art. Preferably, blood cells according to the invention are peripheral blood mononuclear cells (PBMCs), more preferably plasmacytoid dendritic cells (pDCs), monocytes or NK cells.

Preferably, in the in vitro method for identifying compounds for increasing, in particular restoring IFN level, in particular type-I IFN level, more particularly IFN-a and/or IFN-β level, in an individual from candidate compounds according to the invention, the CXCR4 receptor is expressed on the surface of cells, such as HEK cells.

The detectable CXCR4 receptor-biding compound according to the invention can be of any type known to one of skilled in the art.

In Silico Experiments

In silico methods for screening compound are well known to one of skilled in the art. The in silico method according to the invention preferably refers to a method for screening compounds from candidate compounds, or for designing compounds, for increasing, in particular restoring, IFN level, in particular type-I IFN level, more particularly IFN-a and/or IFN-β level, in an individual via bioinformatics tools.

In silico method according to the invention can be of any type known to one of skilled in the art such as docking, for instance using a software such as cDocker, receptor dependent-quantitative structure-activity relationship (RD QSAR), quantitative structure-activity relationship (QSAR), quantitative structure-property relationship (QSPR), pharmacophore model and design de novo.

Preferably, the in silico method for screening compounds from candidate compounds, or for designing compounds, for increasing, in particular restoring, IFN level, in particular type-I IFN level, more particularly IFN-a and/or IFN-β level, in an individual according to the invention is an in silico docking experiments. For example, the in silico method for screening compounds from candidate compounds, or for designing compounds, for increasing, in particular restoring, IFN level, in particular type-I IFN level, more particularly IFN-a and/or IFN-β level, in an individual according to the invention can be performed by using the crystal structure of CXCR4 with a ligand, notably AMD3100, and then identifying the potential biding pocket on the CXCR4 extracellular domain.

Preferably, the designed compound or a candidate compound according to the invention interacts with at least 6 amino acids of a CXCR4 receptor represented by SEQ ID NO: 1, wherein the amino acids are selected from the group consisting of alanine 175, aspartic acid 171, aspartic acid 262, phenylalanine 174, valine 196, glycine 207, tyrosine 255, tyrosine 256, isoleucine 259, serine 263 and glutamic acid 288.

The invention will be further described by the following non-limiting figures and Example.

DESCRIPTION OF THE FIGURES

FIG. 1

FIG. 2

FIGS. 3A, 3B and 3C

EXAMPLE

A. Materials and Methods

1. Blood Samples, Isolation and Culture of Blood Leukocytes.

Blood was obtained from healthy HIV-1-seronegative blood bank donors. Experimental procedures with human blood were done according to the European Union guidelines and the Declaration of Helsinki. In vitro experiments were performed using human peripheral blood mononuclear cells (PBMC) isolated by density centrifugation from peripheral blood leukocyte separation medium (Cambrex, Gaithersburg, Md.). pDC were purified by negative selection with the Human plasmacytoid DC enrichment kit (StemCell Technologies). Cells were cultured in RPMI 1640 (Invitrogen, Gaithersburg, Md.) containing 10% fetal bovine serum (Hyclone, Logan, Utah). After purification, the purity obtained was higher than 91% for pDC.

2. Viral Stimulation and Infection.

PBMC were seeded at $1.10^6/1$ mL or purified pDC were seeded at $5.10^4/100$ µl and then stimulated with the following viruses: inactivated AT-2 HIV-$1_{MN}$ (CXCR4 co-receptor specific) or AT-2 HIV-$1_{ADA}$ (CCR5 co-receptor specific) at 60 ng/mL $p24^{CA}$ equivalent (provided by J.D. Lifson (SAIC-NCI, Frederick, Md.)), Infectious human Influenza A/PR/8/34 virus (Flu), titer 1:8192 at dilution 1:1000 or DENV-2 16681 at MOI 10. Infectious HIV-$1_{MN}$ [tissue culture 50% infective dose (TCID50)=106] and HIV-$1_{ADA}$ (TCID50=1, 000) were used at the same concentration. Purified pDC were pre-treated with amino compounds for 1 hour, following overnight stimulation with virus. Supernatants were collected for cytokine detection. Microvesicles isolated from uninfected cell cultures matched to the culture to produce the virus were used as negative control (Mock).

3. Chemical Compounds.

Histamine dihydrochloride and clobenpropit dihydrobromide (Sigma-Aldrich, Mo., USA) were diluted in pure water. The compounds were added in pDC cultures at 10 µM (or other if specified) 1 hour before stimulation or not of the different viruses. For histamine, X-vivo culture media (Lonza) was used in order to avoid histaminases. Cells were pre-incubated 1 hour with AMD3100 (20 µM) (Sigma-Aldrich, Mo., USA) prior to CB or histamine incubation. pDC were cultured in the presence of 5 mM of the oligodinucleotide A151 (TTAGGG) ODN (Integrated DNA Technologies, Coralville, Iowa).

4. Cytokine Detection.

pDC's supernatants were tested for multispecies soluble IFN-a by ELISA (PBL Assay Science, NJ, USA) according to the manufacturer's instructions.

5. RT-qPCR Analysis.

Total RNA was extracted using RNeasy Micro kit and was submitted to DNase treatment (Qiagen), following manufacturer's instructions. RNA concentration and purity were evaluated by spectrophotometry (Biophotometer, Eppendorf). Five hundred ng of RNA were reverse-transcribed using PrimeScript RT Reagent Kit (Perfect Real Time, Takara) in a 10 µl reaction. Real-time PCR reactions were performed in duplicates using Takyon ROX SYBR MasterMix blue dTTP (Eurogentec) on a 7900HT Fast Real-Time PCR System (Applied Biosystems). Transcripts were quantified using the following program: 3 min at 95° C. followed by 35 cycles of 15 s at 95° C., 20 s at 60° C. and 20 s at 72° C. Values for each transcript were normalized to expression levels of RPL13A (60S ribosomal protein L13a) using the 2-ΔΔCt method. Primers used for quantification of transcripts by real time quantitative PCR are indicated below:

| Gene | Forward primer sequence (5'->3') | Reverse Primer sequence (5'->3') | Size (bp) |
|---|---|---|---|
| TRAIL | GCTGAAGCAGATGCAGGACAA (SEQ ID NO: 2) | TGACGGAGTTGCCACTTGACT (SEQ ID NO: 3) | 135 |
| IFN-α1/13[1] | CCAGTTCCAGAAGGCTCCAG (SEQ ID NO: 4) | TCCTCCTGCATCACACAGGC (SEQ ID NO: 5) | 174 |
| IFN-α4/10[2]v | CCCACAGCCTGGGTAATAGGA (SEQ ID NO: 6) | CAGCAGATGAGTCCTCTGTGC (SEQ ID NO: 7) | 210 |
| IFN-β | TGCATTACCTGAAGGCCAAGG (SEQ ID NO: 8) | AGCAATTGTCCAGTCCCAGTG (SEQ ID NO: 9) | 152 |
| IFN-γ | GGCAGCCAACCTAAGCAAGAT (SEQ ID NO: 10) | CAGGGTCACCTGACACATTCA (SEQ ID NO: 11) | 17 |
| IL6 | TAACCACCCCTGACCCAACC (SEQ ID NO: 12) | ATTTGCCGAAGAGCCCTCAG (SEQ ID NO: 13) | 14 |
| ISG56 | AGGACAGGAAGCTGAAGGAG (SEQ ID NO: 14) | AGTGGGTGTTTCCTGCAAGG (SEQ ID NO: 15) | 19 |

[1]Primers amplify both IFN-a1 and IFN-a13 transcripts
[2]Primers amplify both IFN-a4 and IFN-a10 transcripts 6. Molecular Modelling of CXCR4 with Various Ligands.

The molecular docking program cDOCKER was used for automated molecular docking simulations and various scoring function were used to rank poses: Jain, cDocker Interaction optimized, Ludi. PDB files were cleaned using the prepare protein protocol of Discovery Studio 4.1, membrane was added according to Im. W algorithm Ligands and their conformer were prepared using prepare ligand protocol after conformation generation. Complexes were selected on the basis of criteria of interacting energy combined with geometrical matching quality as well as compromise of scoring function Figures were generated with Discovery studio 4.1 graphics system. The 2D representations of molecular structures interaction of Discovery Studio was used for delineation of the detailed interactions between ligands and CXCR4 (PDB code: 3ODU). An interaction was considered a hydrophobic interaction if the Van der Walls fraction was 0.7 and was considered a hydrogen bond if it was between a listed donor and acceptor and the angles and distances formed by the atoms surrounding the hydrogen bond lay within the default criteria. RMSD were calculated using Discovery studio 4.1 and with ITlt in CXCR4/ITlt co-crystal as reference (PDB code 3ODU).

7. Statistical Analysis.

P values (P) were determined using a two-tailed Student's t test. P<0.05 was considered statistically significant. *=P<0.05; =P<0.01 and *=P<0.001. Univariate distributions of flow cytometry data were performed by probability binning, in 300 bins using FlowJo software.

Data sets were analysed by two-way ANOVA with Bonferroni post-tests (cytokine concentration time courses). GraphPad Prism 5 (GraphPad Software, San Diego, Calif.) was used for data analysis and preparation of all graphs. P-values less than 0.01 were considered to be statistically significant.

RESULTS

1. AMD3100 Prevents Type I Interferon Production Inhibition Induced by Amines 1.1. AMD3100 was tested for inhibition of type I interferon production by HIV-stimulated pDC. AMD3100 alone did not block type I IFN nor TRAIL expression by HIV-activated pDC.

1.2. AMD3100 was then tested for its ability to block the action of amine-type compounds, i.e. histamine and clobenpropit (CB), which bind at the IT1t pocket on CXCR4 (IT1t is a CXCR4 antagonist) and notably inhibit the production of IFN-I by HIV-stimulated pDC.

The expressions of TRAIL, IFN-a and IFN-β in pDC treated or not with AMD3100 were thus quantified.

Purified cells were pre-incubated with AMD3100 for 1 hour and then by histamine or CB for 1 hour and finally exposed to HIV-1 overnight.

Figure 1:
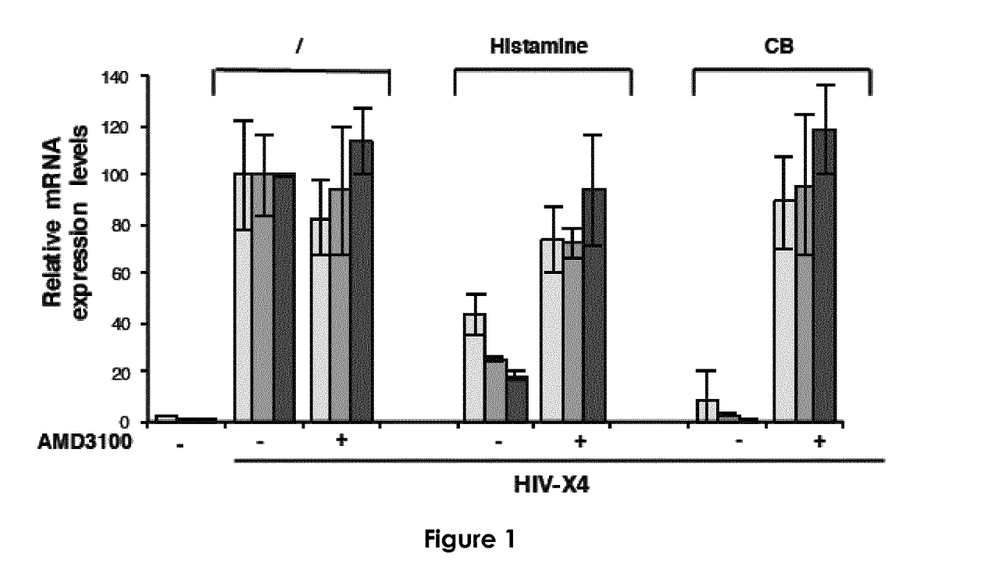
FIG. 1 represents the measure of mRNA levels of TRAIL (first bar), IFN-a (second bar) and IFN-β (third bar) from purified pDC pre-incubated with AMD 3100 (20 μM) then histamine or CB (10 μM) and stimulated overnight with HIV-X4 by RT-qPCR and normalized to RPL13A.
Figure 2:
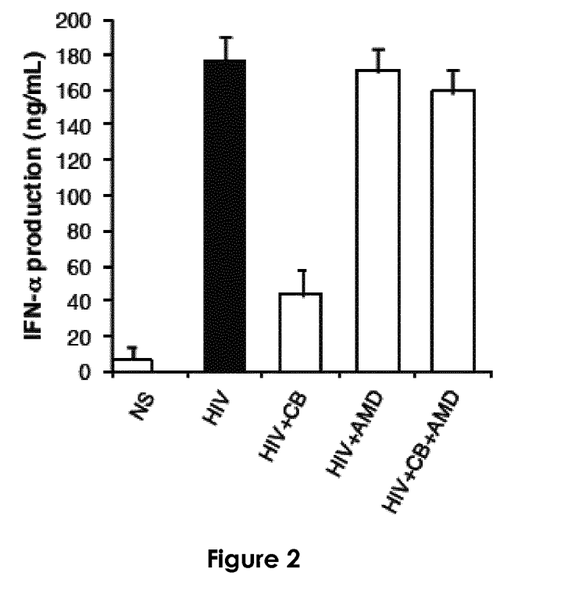
FIG. 2 represents the measure of IFN-a (ng/ml) by ELISA in supernatants of isolated pDC pre-treated with AMD3100 (20 μM), then CB and stimulated with HIV overnight.
Figure 3A:
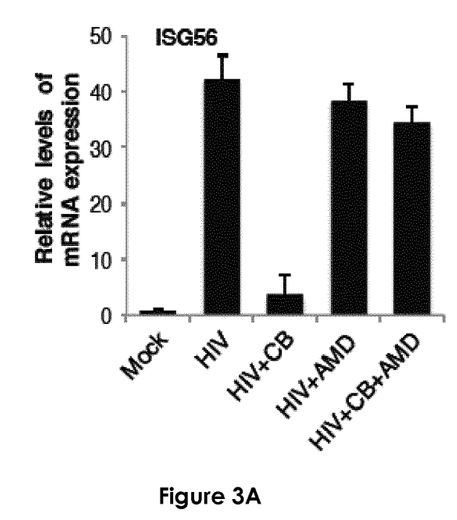
FIGS. 3A-3C represent the measure of mRNA levels of ISG56 (FIG. 3A), IFN-a/β (FIG. 3B) and IL-6 (FIG. 3C) from purified pDC pre-incubated with AMD-3100 (20 μM) then CB (10 μM) and stimulated overnight with HIV, by RT-qPCR and normalized to RPL13A.
Figure 3B:
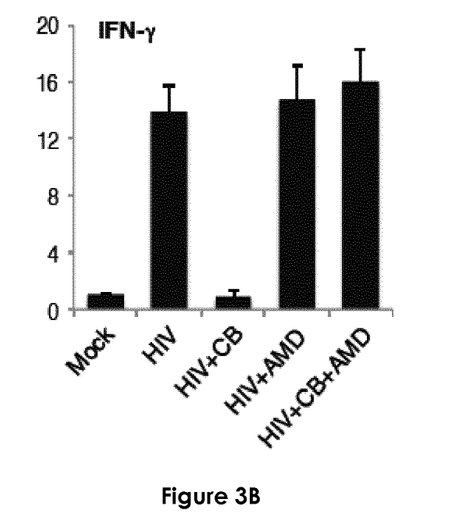
Figure 3C:
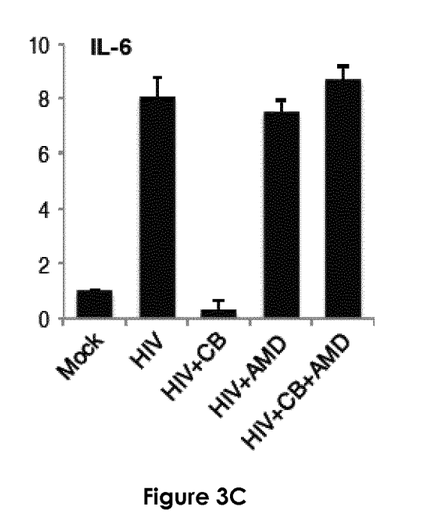

AMD3100 drastically abolished biological activities of histamine and CB on HIV activated-pDC. Indeed, the inventors observed that AMD3100 treatment could restore IFN-a, IFN-β and TRAIL mRNA expression (FIG. 1) and IFN-a production (FIG. 2) inhibited by histamine or CB in HIV-activated pDC. These results were confirmed for the expression of IFN-γ, IL-6 and IFN-stimulated gene 56 (ISG56) mRNA expression in HIV-activated pDC (FIGS. 3A-3C).

2. Identification of a Binding Pocket for AMD3100 on CXCR4 Extracellular Domain

To understand the molecular interaction between AMD3100 and CXCR4, in silico docking experiments were performed.

IT1t, a CXCR4 antagonist, was used as an internal control to validate the molecular modelling protocol. IT1t and AMD3100 were thus docked in the IT1t binding pocket of CXCR4.

It has been first confirmed that IT1t was replaced properly compared to the crystal structure. Indeed, RMSDs of IT1t heavy atoms resolved in crystal structure (PDB code 3ODU) and IT1t docking poses after scoring are around 1 Å (equivalent to the variation observed when comparing IT1t in 3ODU co-crystal with other co-crystallized structures (PDB codes 3OE6-3OE8-3OE9)) (Table 1).

TABLE 1

Validation of docking protocol. Scoring of IT1t poses after docking in CXCR4 (PDB code: 3ODU) using cDocker. Poses were ranked depending on their scores calculated either with Jain, cDocker Interaction Optimized or Ludi as scoring function. RMSD between each top poses and crystallized IT1t as reference was calculated in Å. RMSD: Root-mean-square deviation.

| | Scoring Function | | | X-ray | |
|---|---|---|---|---|---|
| | Jain | cDocker Interaction Optimized | Ludi | IT1t (PDB code 3ODU) vs IT1t in other structures (PDB codes: 3OE6-3OE8-3OE9) | |
| Top pose | RMSD heavy atoms | RMSD heavy atoms | RMSD heavy atoms | PDB code | RMSD heavy atoms |
| #1 | 1.0603 | 1.0603 | 1.0603 | 3OE6 | 0.3887 |
| #2 | 0.7775 | 0.9667 | 0.7775 | 3OE8 | 0.6986 |
| #3 | 0.9667 | 3.8033 | 0.9667 | 3OE9 | 0.6739 |

The 2D representation was used for delineation of the detailed interactions between ligands and CXCR4 (Table 2).

The molecular docking of AMD3100 and CXCR4/IT1t co-crystallization allowed the identification of two distinct binding pockets on CXCR4; AMD3100 pocket covers up superficially the two subpockets of CXCR4 while the IT1t pockets is located more deeply in the minor subpocket of CXCR4. Thus, the access of IT1t or amine-type compounds, such as histamine or CB, to the binding pocket could be blocked by AMD3100.

TABLE 2

Residues involved in ligand binding in IT1T and AMD3100 pockets

| IT1T Binding pocket | | | AMD3100 Binding pocket | | | |
|---|---|---|---|---|---|---|
| | IT1T | CB | AMD3100 | | AMD3100 | CB | IT1t |
| W94 | X | X | | D171 | X | | |
| D97 | X | X | | F174 | X | | |
| W102 | X | X | | A175 | X | | |
| V112 | X | | | V196 | X | | |
| Y116 | X | X | | G207 | X | | |
| R183 | X | X | | Y255 | X | X | X |
| I185 | X | X | | Y256 | X | | |
| C186 | X | X | | I259 | X | X | |
| D187 | X | X | | D262 | X | | |
| Y190 | | X | | S263 | X | | |
| E288 | X | X | X | E288 | X | X | X |

The invention claimed is:

1. A method for increasing or restoring interferon (IFN) level in an individual in need thereof, the method comprising administering to the individual a CXCR4 receptor-binding compound, wherein the interferon is a type-I interferon (IFN-I), and wherein the CXCR4 receptor-binding compound is plerixafor.

2. The method according to claim 1, wherein the CXCR4 receptor-binding compound interacts with at least 6 amino acids of a CXCR4 receptor represented by SEQ ID NO: 1, wherein the amino acids are selected from the group consisting of alanine 175, aspartic acid 171, aspartic acid 262, phenylalanine 174, valine 196, glycine 207, tyrosine 255, tyrosine 256, isoleucine 259, serine 263 and glutamic acid 288.

3. The method according to claim 1, wherein the interferon (INF) is IFN-α and/or IFN-β.

4. The method according to claim 1, for increasing or restoring IFN secretion by immune cells.

5. The method according to claim 1, for increasing or restoring IFN secretion by immune cells selected from the group consisting of plasmacytoid dendritic cells, monocytes and NK cells.

6. The method according to claim 1, for preventing or treating a disease selected from the group consisting of a viral infection, an opportunistic infection, allergy, rheumatoid arthritis, multiple sclerosis, a cancer with an overproduction of spermine, depression-induced immunosuppression and diabetes.

7. A method for increasing or restoring type-I IFN secretion by immune cells comprising the in vitro use of a CXCR4 receptor-binding compound as defined in claim 1.

* * * * *